United States Patent [19]

Buonafede

[11] Patent Number: 5,129,916
[45] Date of Patent: Jul. 14, 1992

[54] SYSTEM AND METHOD FOR DRIVING VENOUS BLOOD FROM BODY EXTREMITY TO PREPARE SAME FOR LOCAL ANESTHETIC

[76] Inventor: Dennis Buonafede, 55 Mulberry La., Huntington, Conn. 06484

[21] Appl. No.: 588,757

[22] Filed: Sep. 27, 1990

[51] Int. Cl.⁵ .............................................. A61B 17/00
[52] U.S. Cl. ............................ 606/201; 128/DIG. 20
[58] Field of Search ................ 606/201, 202, 203; 128/DIG. 20, 82, 157

[56] References Cited

U.S. PATENT DOCUMENTS

| | | | |
|---|---|---|---|
| 2,582,648 | 1/1952 | Mowbray | 128/82 |
| 2,832,336 | 4/1958 | Davis et al. | 128/DIG. 20 |
| 3,186,404 | 6/1965 | Gardner | 606/201 |
| 3,785,374 | 1/1974 | Lipson | 128/82 |
| 3,824,992 | 7/1974 | Nicholson et al. | 128/DIG. 20 |
| 4,066,084 | 1/1978 | Tillander | 128/327 |
| 4,098,268 | 7/1978 | Scott | 128/82 |
| 4,153,054 | 5/1979 | Boone | 128/157 |
| 4,228,792 | 10/1980 | Rhys-Davies | 128/24.3 |
| 4,406,281 | 9/1983 | Hubbard et al. | 606/203 |
| 4,442,834 | 4/1984 | Tucker et al. | 128/DIG. 20 |
| 4,610,245 | 9/1986 | Biearman | 128/82 |
| 4,781,189 | 11/1988 | Vijil-Rosales | 128/327 |
| 4,848,324 | 7/1989 | Gavriely | 606/203 |
| 5,083,557 | 1/1992 | Lennon et al. | 128/157 |

FOREIGN PATENT DOCUMENTS 840452  4/1939  France ........................ 128/DIG. 20

OTHER PUBLICATIONS

Brown, Donald B. and Ian F. Kerr, "Pneumatic Bandage for Use in the Stripping of Varicose Veins," *Lancet*, vol. 1, No. 7330, Feb. 22, 1964, pp. 415, 416.

*Primary Examiner*—C. Fred Rosenbaum
*Assistant Examiner*—William Lewis
*Attorney, Agent, or Firm*—CTC & Associates

[57] ABSTRACT

A two piece system and method for driving venous blood from a patient's extremity to prepare the same for local anesthetic. The first piece is a flexible protective undersleeve and the second a flexible pneumatic outer sleeve. Both sleeves have a closed end and an open end for insertion of the body extremity. The protective sleeve is first applied over the body extremity followed by deflated pneumatic outer sleeve. The pneumatic sleeve is then inflated to drive venous blood from the extremity. A tourniquet, which may be the well known proximal and distal cuffs is applied to disrupt arterial blood flow. The pneumatic sleeve is then deflected and removed from the upper body extremity as is the protective undersleeve prior to the administration of local anesthetic.

5 Claims, 2 Drawing Sheets

SYSTEM AND METHOD FOR DRIVING VENOUS BLOOD FROM BODY EXTREMITY TO PREPARE SAME FOR LOCAL ANESTHETIC

BACKGROUND OF THE INVENTION

This invention relates to a system for driving blood from a patient's body extremity or limb to prepare same for a local anesthetic.

The desirability of driving blood from a body extremity or limb prior to administration of a local anesthetic is well known.

A patentability search hereon has revealed the following U.S. patents:

| U.S. Pat. No. | Date | Inventor |
| --- | --- | --- |
| 3,785,374 | January 15, 1974 | Lipson |
| 4,066,084 | January 3, 1978 | Tillander |
| 4,098,268 | July 4, 1978 | Scott |
| 4,228,792 | October 21, 1980 | Rhys-Davies |
| 4,610,245 | September 9, 1986 | Biearman |
| 4,781,189 | November 1, 1988 | Vijil-Rosales |

The patents to Lipson, Scott and Bierarman do not appear to be concerned with driving blood from a limb.

Tillander is a blood emptying device for pressing blood from an extremity toward the heart. A number of sections are arranged around the extremity which are to be filled with a gaseous medium. A valve between adjacent pairs of sections allows a first section to fill to a predetermined pressure before the second section fills.

Rhys-Davies discloses an exsanguinating device for displacing blood from a limb by compression. A double-walled tube of elastomeric material is filled with fluid and is rolled along a patient's limb with the two walls exchanging positions.

Vijil-Rosales teaches a device for exsanguinating a limb using an inflatable bladder which surrounds the limb. The bladder is inflated to evacuate the blood from the limb.

A system according to the instant invention is essentially a tow-piece system, the two pieces being a pneumatic sleeve and a protective undersleeve. The sleeves are flexible to conform to the patient's extremity and the protective undersleeve protects the clinician from infection. The diameter and length of both sleeves are determined by the patient's size so as to be easily applied to the patient's extremity without interfering with open wounds or previously emplaced intravenous devices. The inventive system offers significant saving in clinicians' time, more reliable emptying of venous blood from patients' extremities and cost reduction, together with less pain to patients.

Important objects of the invention are to provide a simple, less patient painful system having the foregoing advantages for driving blood from a patient's extremity to prepare same for local anesthetic. These and other objects and advantages of the invention will appear hereinafter.

SUMMARY OF THE INVENTION

The inventive system comprises a pneumatic sleeve and a disposable undersleeve. Both sleeves are of flexible material.

The pneumatic sleeve has an inner wall and an outer wall with a sealed annular chamber therebetween. An air valve is in the outer wall whereby air can be introduced into the sealed chamber to inflate the pneumatic sleeve, or removed from the sealed chamber to deflate the pneumatic sleeve. The pneumatic sleeve has a closed end provided with a handle with holes whereby the pneumatic sleeve can be manipulated and hung from a support and an open end for receiving the patient's extremity. Similarly, the undersleeve is generally cylindrical and is open at one end.

In use, the undersleeve is applied to the extremity and the pneumatic sleeve is applied, in deflated condition, over the undersleeve. The pneumatic sleeve is then inflated to a pressure in excess of the pressure of the venous blood to drive same from the extremity. A tourniquest is applied to disrupt arterial blood flow and the pneumatic sleeve and the undersleeve are removed prior to administration of local anesthetic, such as Bier Block.

A modified pneumatic sleeve is disclosed for use with the well known proximal cuff and distal cuff tourniquet to disrupt arterial blood flow. The modified pneumatic sleeve is provided with a pair of slits that are parallel to the axis of the modified pneumatic sleeve and are in open communication with the open end of the modified sleeve and are adapted to receive therein tubular inlets/outlets of the proximal cuff and the distal cuff.

The modified pneumatic sleeve has two flaps with Velcro thereon, and complementary Velcro elements are also provided on the modified sleeve itself to engage the Velcro on the flaps to hold the modified pneumatic sleeve in surrounding relationship with the proximal cuff and the distal cuff.

DESCRIPTION OF THE INVENTION

Figure 1:
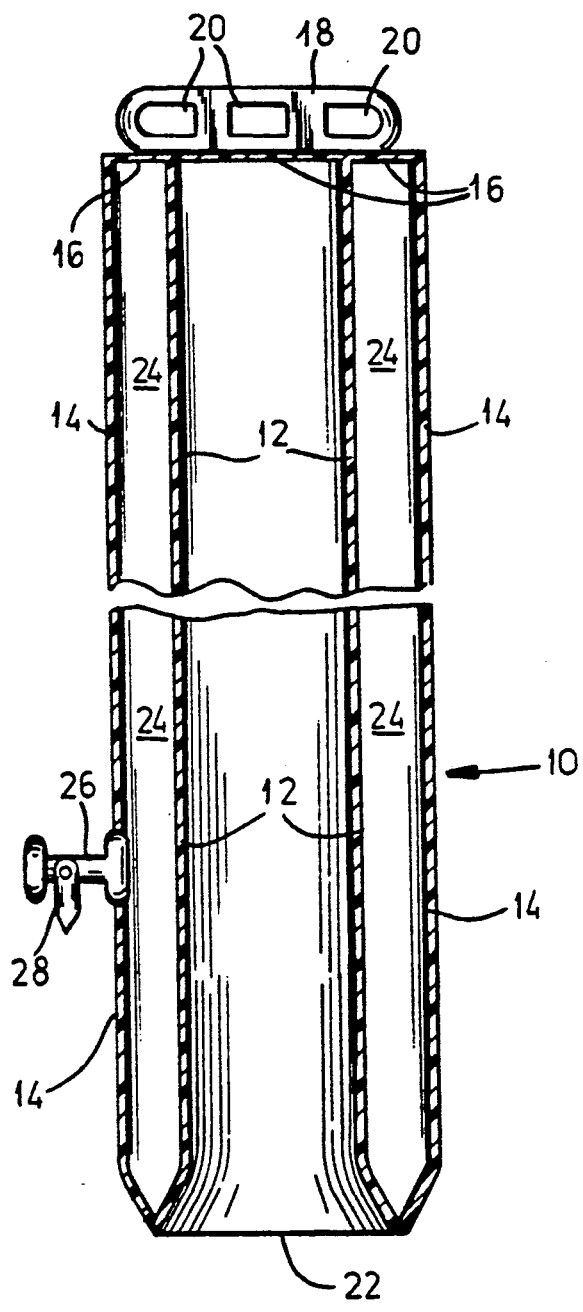
FIG. 1 is a broken away axial sectional view of a pneumatic sleeve that is a component of a system embodying the invention.

FIG. 1 shows a pneumatic sleeve 10 that is a component of a system embodying the invention. Sleeve 10 is of flexible material such as known suitable plastic materials and will be described as far as its shape is concerned in its inflated condition, but it is to be understood that in its uninflated condition sleeve 10 is more or less collapsed.

Pneumatic sleeve 10 has an inner cylindrical wall 12 and an outer cylindrical wall 14 coaxial with wall 12. Sleeve 10 has an imperforate closed end 16 closing surfaces 12 and 14. Sleeve 10 also has a handle 18 affixed to and protruding from closed end 16. Handle 18 has finger holes 20 which facilitate manipulating sleeve 10 and which also provide means for hanging sleeve 10 from a support.

Pneumatic sleeve 10 also has an open end 22 at the axial end remote from closed end 16. Inner and outer cylindrical walls 12 and 14 are sealed together at open end 22, thereby to create an annular sealed chamber 24 between inner and outer cylindrical walls 12 and 14 and extending from closed end 16 to open end 22.

Lastly, pneumatic sleeve 10 has air valve 26 in outer wall 14 at a location spaced from ends 16 and 22 but somewhat closer to end 22. Valve 26 has a lever 28 that is movable between a closed position and an open position in which sleeve 10 can be inflated or deflated.

Figure 2:
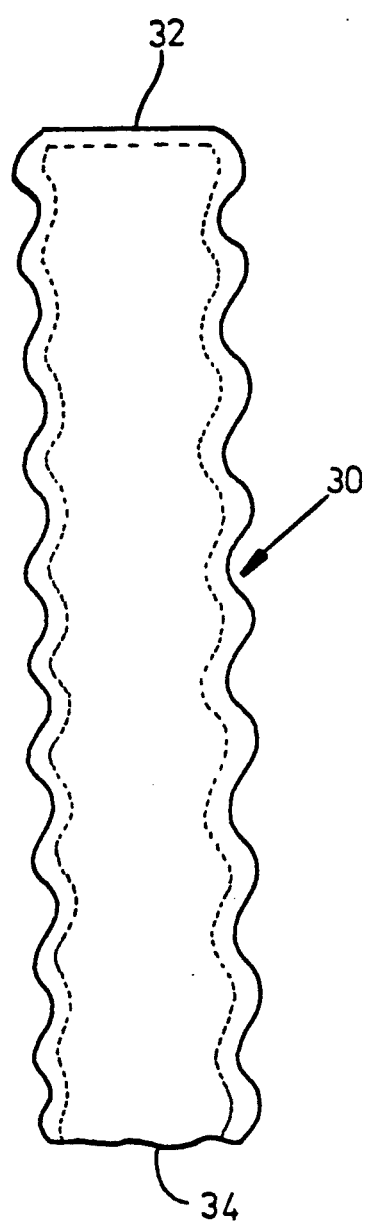
FIG. 2 is a longitudinal axial elevation of an undersleeve that is another component of the system.

A protective undersleeve 30 is illustrated in FIG. 2. Undersleeve 30 is another component of the system and is also of flexible material such as known suitable flexible plastic materials. Undersleeve 30, which is generally cylindrical, is closed at one end 32 and is open at end 34. Undersleeve 30 is disposable.

The system presented by sleeves 10 and 30 is for use in preparing an upper extremity of a patient for local anesthetic. To do this, the proximal and distal cuffs are applied to the patient's extremity nearest the torso. Undersleeve 30 is applied to the extremity and pneumatic sleeve 10 is applied over undersleeve 30. Air is pumped into valve 26 (with lever 28 in the open position) and into sealed chamber 24 to inflate sleeve 10 to a pressure in excess of the pressure of the venous blood to drive the same from the extremity. When venous blood is driven from the patient's extremity, the proximal and distal cuffs are inflated to disrupt arterial blood flow. Pneumatic sleeve 10 is deflated. It and undersleeve 30 are removed prior to administration of local anesthetic, such as a Bier Block.

As mentioned, sleeves 10 and 30 are flexible and thus conform readily to the extremity, while protective undersleeve 30 protects the clinician from infection. Also, the inventive system appears to offer significant saving in clinicians' time, more reliable emptying of venous blood and cost reduction, together with less pain to the patient.

Figure 3:
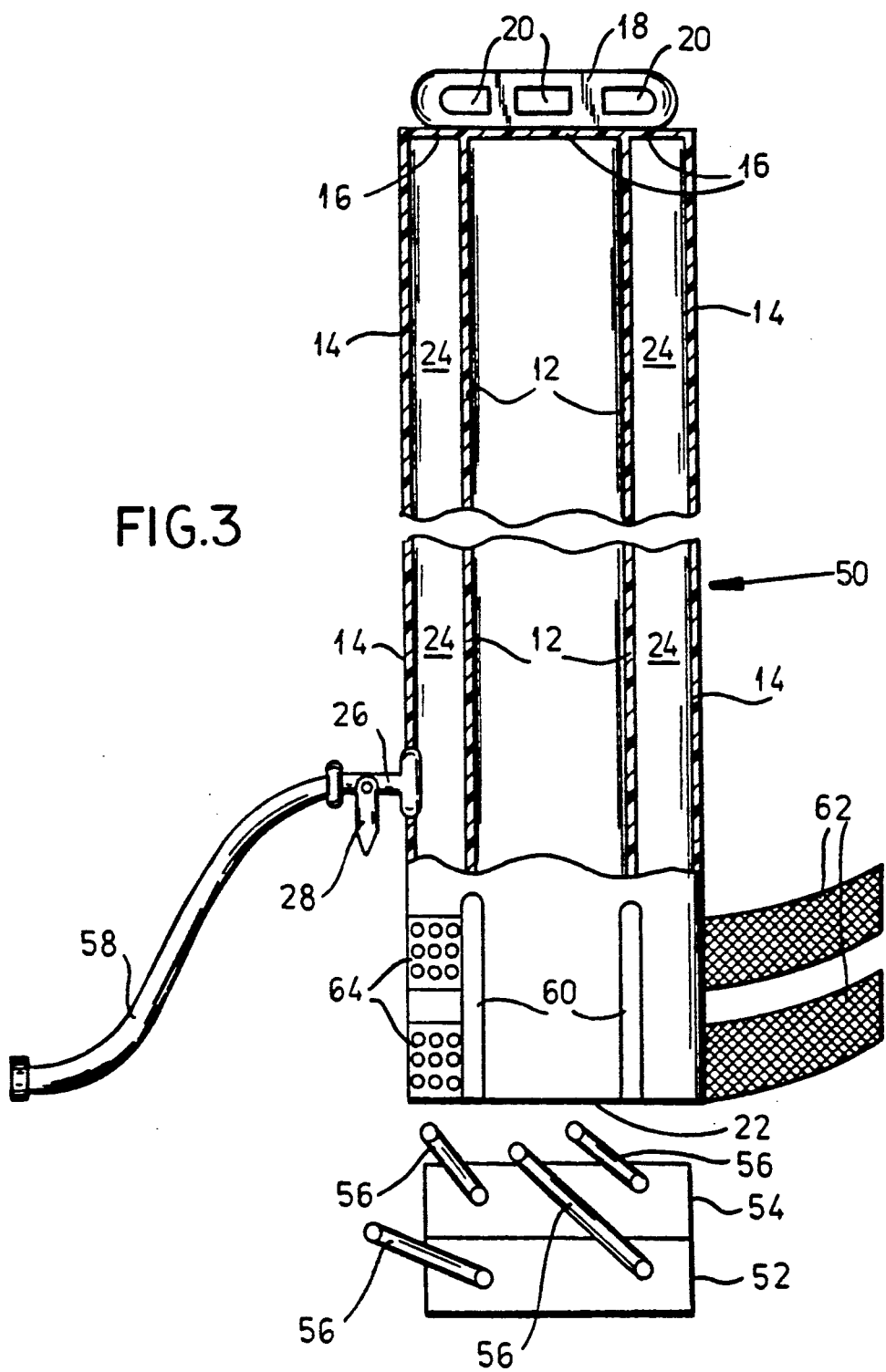
FIG. 3 is a view similar to FIG. 1 but showing a modified pneumatic sleeve that is a component of a modified system embodying the invention and also showing the modified pneumatic sleeve connected to a source of air pressure, and further showing proximal and distal cuffs.

FIG. 3 shows a modified pneumatic sleeve 50 many parts of which are the same as corresponding parts of pneumatic sleeve 10, the parts bearing the same reference numerals being the same. The differences between pneumatic sleeve 10 and pneumatic sleeve 50 will be described shortly.

FIG. 3 also illustrates a well known proximal cuff 52 and a well known distal cuff 54. Each of cuffs 52 and 54 has two inlets/outlets 56 in the form of protruding tubes. Inlets/outlets 6 are controlled by a special known monitor/pressure machine (not shown). The patient's extremity is raised, proximal cuff 52 is placed and distal cuff 54 is placed.

Disposable undersleeve 30 is pulled over the patient's extremity and pneumatic sleeve 50 is pulled over undersleeve 30 and inflated by pumping air through a hose 58 and through valve 26 and into sealed chamber 24.

To revert to pneumatic sleeve 50, it is provided with a pair of slits 60 that are parallel to the axis of sleeve 50 and in open communication with open end 22 and adapted to receive therein inlets/outlets 56 of cuffs 52 and 54, with an inlet/outlet 56 of each of cuffs 52 and 54 being in each slit 60, and with pneumatic sleeve 50 covering cuffs 52 and 54. Pneumatic sleeve 50 is also provided with two flaps 62 with Velcro thereon. Complementary Velcro elements 64 are provided on pneumatic sleeve 50 to engage the Velcro on flaps 62 to hold pneumatic sleeve 50 in surrounding relationship with cuffs 52 and 54. Flaps 62 are spaced from each other, so that inlets/outlets 56 of proximal cuff 52 will lie between flaps 62 when flaps 62 are in engagement with complementary Velcro elements 64.

After pneumatic sleeve 50 is inflated as aforesaid, forcing the venous blood from the extremity, the proximal and distal cuffs are inflated to disrupt arterial blood flow. When this is complete the pneumatic sleeve 50 and undersleeve 30 are removed. Local anesthetic is then infused to effect the Bier Block.

It is evident that the inventive system attains the stated objects and advantages, among others.

The disclosed details are exemplary only and are not to be taken as limitations on the invention, except as those details may be included in the appended claims.

What is claimed is:

1. A two piece pneumatic system for driving venous blood from a patient's body extremity to prepare same for local anesthetic, said system comprising a flexible, disposable, conformable undersleeve and a reusable conformable pneumatic outer sleeve, both said undersleeve and said outer sleeves being closed at one end and open at the other end for receiving said patient's extremity, said inner sleeve acting to cover said patient's extremity to protect a clinician from infection, said pneumatic outer sleeve being provided with a handle with holes whereby it can be manipulated and hung from a support, said pneumatic sleeve having an inner wall and an outer wall with a sealed annular chamber therebetween and an air valve in said outer wall for introducing and removing air from said sealed annular chamber to inflate said annular chamber to drive blood from said patient's extremity and to deflate said annular chamber to ease the removal of said pneumatic sleeve when venous blood has been driven from said extremity.

2. A system according to claim 1 wherein said inner wall and said outer wall of said outer pneumatic sleeve are sealed together at said open end and said closed end.

3. A system according to claim 1 for use with a proximal cuff and a distal cuff, said pneumatic sleeve having a pair of slits parallel to its axis and in open communication with said open end of said pneumatic sleeve, said slits adapted to receive therein tubular inlets/outlets of the proximal cuff and the distal cuff and said pneumatic sleeve also having two flaps with Velcro thereon and complementary Velcro elements on the exterior of said outer wall to engage the Velcro on said flaps, thereby to hold said pneumatic sleeve in surrounding relationship with said proximal cuff and the distal cuff.

4. A method in combination with the system according to claim 3 to remove venous blood from a patient's extremity and to protect the administering clinician from contact with said extremity prior to the administration of anesthetic which comprises applying a tourniquet such as said inflatable proximal and said distal cuffs on said patient's extremity nearest the torso; applying said flexible plastic undersleeve over said extremity below said proximal and distal cuffs; applying said pneumatic sleeve over said undersleeve; pressurizing and inflating said pneumatic sleeve to a pressure in excess of the pressure of said venous blood thereby draining the same from the extremity, inflating said proximal and distal cuffs to disrupt arterial blood, deflating said pneumatic sleeve, removing said deflated pneumatic sleeve and removing said undersleeve, said extremity now being ready for the administration of anesthetic.

5. A system according to claim 1 wherein said undersleeve and said pneumatic outer sleeve are made from flexible plastic materials.

* * * * *